(12) United States Patent
Borgia et al.

(10) Patent No.: US 9,753,037 B2
(45) Date of Patent: Sep. 5, 2017

(54) BIOMARKER PANEL FOR DETECTING LUNG CANCER

(71) Applicant: Rush University Medical Center, Chicago, IL (US)

(72) Inventors: Jeffrey A. Borgia, Chicago, IL (US); Michael Liptay, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 58 days.

(21) Appl. No.: 14/206,486

(22) Filed: Mar. 12, 2014

(65) Prior Publication Data
US 2014/0274772 A1    Sep. 18, 2014

Related U.S. Application Data

(60) Provisional application No. 61/792,710, filed on Mar. 15, 2013.

(51) Int. Cl.
*G01N 33/574*    (2006.01)

(52) U.S. Cl.
CPC ... *G01N 33/57423* (2013.01); *G01N 2333/54* (2013.01); *G01N 2333/555* (2013.01); *G01N 2800/60* (2013.01)

(58) Field of Classification Search
None
See application file for complete search history.

(56) References Cited

U.S. PATENT DOCUMENTS

| | | |
|---|---|---|
| 2003/0219768 A1 | 11/2003 | Beebe |
| 2004/0091857 A1 | 5/2004 | Nallur |
| 2008/0160546 A1 | 7/2008 | Colpitts et al. |
| 2009/0047689 A1 | 2/2009 | Kolman |
| 2009/0176228 A1 | 7/2009 | Birse et al. |
| 2009/0233268 A1 | 9/2009 | Lin et al. |
| 2010/0009386 A1 | 1/2010 | Streeper et al. |
| 2010/0119537 A1 | 5/2010 | Podack |
| 2010/0152058 A1 | 6/2010 | Di Fiore et al. |
| 2010/0240081 A1 | 9/2010 | Rollinger et al. |
| 2012/0094863 A1 | 4/2012 | Stroh |
| 2012/0115745 A1 | 5/2012 | McKeegan et al. |
| 2013/0225442 A1 | 8/2013 | Borgia |

FOREIGN PATENT DOCUMENTS

| | | |
|---|---|---|
| WO | WO 03/000928 A2 | 1/2003 |
| WO | WO 2009/028580 A1 | 3/2009 |
| WO | WO 2009/067546 A2 | 5/2009 |

OTHER PUBLICATIONS

Farlow et al, British J Can, 2010, 103:1221-8, IDS # A11, filed on Dec. 15, 2015.*
Borgia et al, J. Thoracic Oncology 4:338-247, 2009, IDS # A6, filed on Dec. 15, 2015.*
Wald et al, JI, 177:6983-6990, 2006.*
SDF-1 antibody fact sheet Bio-Rad, 2016.*
Aberle DR et al.; "Reduced Lung-Cancer Mortality with Low-Dose Computed Tomographic Screening"; The New England Journal of Medicine, vol. 365, No. 5; Aug. 4, 2011; pp. 395-409.
Bach PB et al.; "Benefits and Harms of CT Screening for Lung Cancer: A Systematic Review"; JAMA, vol. 307, No. 22; Jun. 13, 2012; pp. 2418-2429.
Bach PB et al.; Screening for Lung Cancer: ACCP Evidence-Based Clinical Practice Guidelines (2nd edition); Chest; Sep. 2007 Supplement; pp. 69S-77S.
Bach PB et al.; "Computed Tomography Screening and Lung Cancer Outcomes"; JAMA, vol. 297, No. 9; Mar. 7, 2007; pp. 953-961.
Bigbee WL et al.; "A Multiplexed Serum Biomarker Immunoassay Panel Discriminates Clinical Lung Cancer Patients from High-Risk Individuals Found to Be Cancer-Free by CT Screening"; Journal of Thoracic Oncology, vol. 7, No. 4; Apr. 2012; pp. 698-708.
Borgia JA et al.; "Establishment of a Multi-Analyte Serum Biomarker Panel to Identify Lymph Node Metastases in Non-Small Cell Lung Cancer"; Journal of Thoracic Oncology, vol. 4, No. 3; Mar. 2009; pp. 338-347.
Boyle P et al.; "Clinical validation of an autoantibody test for lung cancer"; Annals of Oncology; Dec. 2011; pp. 383-389.
Breiman L; "Random Forests"; Machine Learning, vol. 45, Issue 1; Oct. 2001; pp. 5-32.
Breiman L et al.; "Classification and Regression Trees"; 36-350, Data Mining; Nov. 6, 2009; 25 pages.
Buccheri G et al.; "Clinical Equivalence of Two Cytokeratin Markers in Non-Small Cell Lung Cancer: A Study of Tissue Polypeptide Antigen and Cytokeratin 19 Fragments"; Chest; Aug. 2003; pp. 622-632.
Farlow EC et al.; "A multi-analyte serum test for the detection of non-small cell lung cancer"; British Journal of Cancer; Sep. 21, 2010; pp. 1221-1228.
Farlow EC et al.; "Development of a Multiplexed Tumor-Associated Autoantibody-Based Blood Test for the Detection of Non-Small Cell Lung Cancer"; Clin Cancer Res; Jul. 1, 2010; pp. 3452-3462.
Field JK et al.; "International Association for the Study of Lung Cancer Computed Tomography Screening Workshop 2011 Report"; Journal of Thoracic Oncology, vol. 7, No. 1; Jan. 2012; pp. 10-19.
Fontana RS et al.; "Lung Cancer Screening: The Mayo Program"; Journal of Occupational Medicine, vol. 28, No. 8; Aug. 1986; pp. 746-750.
Goldstraw P et al.; "The IASLC Lung Cancer Staging Project: Proposals for the Revision of the TNM Stage Groupings in the Forthcoming (Seventh) Edition of the TNM Classification of Malignant Tumours"; Journal of Thoracic Oncology, Vo. 2, No. 8; Aug. 2007; pp. 706-714.

(Continued)

*Primary Examiner* — Lei Yao
(74) *Attorney, Agent, or Firm* — Brinks Gilson & Lione

(57) ABSTRACT

A method and a kit for assessing risk of lung cancer versus benign disease in a subject are provided. The method includes obtaining a biological sample from the subject and determining a measurement for a panel of biomarkers in the biological sample. The panel includes at least two biomarkers selected from the group consisting of IL-6, IL-1ra, IL-10, SDF-1α+β, TNF-α, MIP-1α, sIL-2Rα, CA-125, sE-Selectin, Eotaxin, sEGFR, MMP-2, OPN, MCP-1, CRP, sICAM-1 and CYFRA 21.1. The method further includes comparing the measurement to a reference profile for the panel of biomarkers, sorting the subject into a group and determining whether the subject is at risk for lung cancer based on the group.

10 Claims, 6 Drawing Sheets

(56) References Cited

OTHER PUBLICATIONS

Goulart BH et al.; "Lung Cancer Screening with Low-Dose Computed Tomography: Costs, National Expenditures, and Cost-Effectiveness"; Journal of the National Comprehensive Cancer Network, vol. 10, No. 2; Feb. 2012; pp. 267-275.
Groome PA et al.; The IASLC Lung Cancer Staging Project: Validation of the Proposals for Revision of the T, N, and M Descriptors and Consequent Stage Groupings in the Forthcoming (Seventh) Edition of the TNM Classification of Malignant Tumours; Journal of Thoracic Oncology, vol. 2, No. 8; Aug. 2007; pp. 694-705.
Henschke CI et al.; "Survival of Patients with Stage I Lung Cancer Detected on CT Screening"; New England Journal of Medicine, vol. 355, No. 17; Oct. 26, 2006; pp. 1763-1771.
Henschke CI et al.; "CT Screening for Lung Cancer: Update 2007"; The Oncologist, vol. 13; Jan. 2008; pp. 65-78.
Kubik A et al.; "Lack of benefit from semi-annual screening for cancer of the lung: follow-up report of a randomized controlled trial on a population of high-risk males in Czechoslovakia"; International Journal of Cancer, vol. 45, Issue 1; Jan. 15, 1990; pp. 26-33.
MacMahon H et al.; "Guidelines for Management of Small Pulmonary Nodules Detected on CT Scans: A Statement from the Fleischner Society"; Radiology; Nov. 2005; pp. 395-400.
Melamed MR et al.; "Screening for early lung cancer. Results of the Memorial Sloan-Kettering Study in New York"; Chest; Jul. 1984; pp. 44-53.
Murray A et al.; "Technical validation of an autoantibody test for lung cancer"; Annals of Oncology, vol. 21, No. 8; Aug. 2010; pp. 1687-1693.
Oken MM et al.; "Screening by Chest Radiograph and Lung Cancer Mortality: The Prostate, Lung, Colorectal, and Ovarian (PLCO) Randomized Trial"; Jama, vol. 306, No. 17; Nov. 2, 2011; pp. 1865-1873.
Pastor A et al.; "Diagnostic value of SCC, CEA and CYFRA 21.1 in lung cancer: a Bayesian analysis"; European Respiratory Journal, vol. 10, Issue 3; Mar. 1, 1997; pp. 603-609.
Patel K et al.; "Enhancement of a multianalyte serum biomarker panel to identify lymph node metastases in non-small cell lung cancer with circulating autoantibody biomarkers"; International Journal of Cancer, vol. 129, Issue 1; Jul. 1, 2011; pp. 133-142.
Patz EF, Jr. et al.; "National Lung Cancer Screening Trial American College of Radiology Imaging Network Specimen Biorepository originating from the Contemporary Screening for the Detection of Lung Cancer Trial (NLST, ACRIN 6654): Design, Intent, and Availability of Specimens for Validation of Lung Cancer Biomarkers"; Journal of Thoracic Oncology, vol. 5, No. 10; Oct. 2011; pp. 1502-1506.
Port JL et al.; "Tumor Size Predicts Survival Within Stage IA Non-Small Cell Lung Cancer"; Chest, vol. 124, No. 5; Nov. 2003; pp. 1828-1833.
Alemàn, M. et al.; "Leptin Role in Advanced Lung Cancer. A Mediator of the Acute Phase Response or a Marker of the Status of Nutrition?"; Cytokine, vol. 19, No. 1; Jul. 7, 2002; pp. 21-26.
American Cancer Society; "Cancer Facts & Figures 2013"; 2013 [cited 2013 Jun. 6, 2013]; 64 pages; Available from: http://www.cancer.org/acs/groups/content/@epidemiologysurveilance/documents/document/acspc-036845.pdf.
Borgia JA et al.; "Prognostic Value of Circulating Angiogenesis Biomarkers in Rapidly Progressing NSCLC"; The joint AACR-IASLC meeting on the Molecular Origins of Lung Cancer, San Diego, CA; Jan. 6-9, 2014; one page.
Brichory, F. et al.; "An immune response manifested by the common occurrence of annexins I and II autoantibodies and high circulating levels of IL-6 in lung cancer"; Proceedings of the National Academy of Sciences of the United States of America, vol. 98, No. 17; Aug. 14, 2001; 9824-9.
Carpagnano, G. et al.; "IL-2, TNF-α, and Leptin: Local Versus Systemic Concentrations in NSCLC Patients"; Oncology Research, vol. 16; Aug. 2007; pp. 375-381.
Fidias PM et al.; "Phase III study of immediate compared with delayed docetaxel after front-line therapy with gemcitabine plus carboplatin in advanced non-small-cell lung cancer"; J Clin Oncol, vol. 27; Feb. 1, 2009; pp. 591-598.
He et al.; "Proteomics-based identification of α-enolase as a tumor antigen in non-small lung cancer"; Cancer Science; vol. 98, No. 8; Aug. 2007; pp. 1234-1240.
Jankowska, R. et al.; "Serum Antibodies to Retinal Antigens in Lung Cancer and Sarcoidosis"; Pathobiology, vol. 71, No. 6; Dec. 2004; pp. 323-328; Abstract.
Jemal A et al.; "Cancer occurrence"; Methods in Molecular Biology, vol. 471: Abstract; 2009; pp. 3-29.
Jemal A. et al.; "Annual report to the nation on the status of cancer 1975-2005, featuring trends in lung cancer, tobacco use, and tobacco control"; J Natl Cancer Inst, vol. 100; Dec. 3, 2008; pp. 1672-1694.
Kaminska et al.; "Pretreatment Serum Levels of Cytokines and Cytokine Receptors in Patients with Non-Small Cell Lung Cancer, and Correlations with Clinicopathological Features and Prognosis"; Oncology, vol. 70; May 2006; pp. 115-125.
Lai, Chun-Liang et al.; "Presence of Serum Anti-p53 Antibodies Is Associated with Pleural Effusion and Poor Prognosis in Lung Cancer Patients"; Clinical Cancer Research, vol. 4; Dec. 1998; pp. 3025-3030.
Seike, Masahiro et al.; "Use of a Cytokine Gene Expression Signature in Lung Adenocarcinoma and the Surrounding Tissue as a Prognostic Classifier"; Journal of the National Cancer Institute, vol. 99, No. 16; Aug. 15, 2007; pp. 1257-1269.
Shersher, David D. et al.; "Biomarkers of the Insulin-Like Growth Factor Pathway Predict Progression and Outcome in Lung Cancer"; Ann Thorac Surg, vol. 92; Jun. 2011; pp. 1805-1811.
Vercillo, M. et al.; "A multi-analyte serum test for the early diagnosis of non-small cell lung cancer"; Journal of Clinical Oncology, vol. 28, No. 15, Supplement; May 20, 2010; p. 1554; Abstract.
Zhu et al.; "Immunohistochemical markers of prognosis in non-small cell lung cancer: a review and proposal for a multiphase approach to marker evaluation"; Journal of Clinical Pathology, vol. 59; Aug. 2006; pp. 790-800.

\* cited by examiner

| # | Variables | IL-6 | IL-1ra | IL-10 | SDF-1(α+β) | TNF-α | MIP-1α | IL-2Rα | CA125 | Eotaxin | sE-Selectin | sEGFR | MMP-2 | Osteopontin | MCP-1 | Misclassification Rate (%) |
|---|---|---|---|---|---|---|---|---|---|---|---|---|---|---|---|---|
| 1 | 14 | × | × | × | × | × | × | × | × | × | × | × | × | × | × | 14.43 |
| 2 | 11 | × | × | × | × | × | × | × | × | × | × | × |   |   |   | 13.40 |
| 3 | 9  | × | × | × | × | × | × | × | × | × |   |   |   |   |   | 13.40 |
| 4 | 7  | × | × | × | × | × | × | × |   |   |   |   |   |   |   | 12.37 |
| 5 | 7  | × | × | × | × | × | × |   |   |   |   |   |   |   |   | 12.37 |
| 6 | 5  | × | × | × | × | × |   |   |   |   |   |   |   |   |   | 13.40 |
| 7 | 4  | × | × | × | × |   |   |   |   |   |   |   |   |   |   | 13.40 |
| 8 | 3  | × | × | × |   |   |   |   |   |   |   |   |   |   |   | 11.34 |
| 9 | 2  | × | × |   |   |   |   |   |   |   |   |   |   |   |   | 11.34 |

FIG. 4

BIOMARKER PANEL FOR DETECTING LUNG CANCER

RELATED APPLICATIONS

This application claims the benefit of U.S. Application Ser. No. 61/792,710, filed Mar. 15, 2013, which is incorporated by reference herein in its entirety.

TECHNICAL FIELD

The present invention relates to a method and a kit for assigning clinical significance to indeterminate lung nodules and for a primary screen in assessing high risk subjects, and in particular to a method and a kit for assigning clinical significance to indeterminate lung nodules or for a primary screen using a biomarker panel for detecting lung cancer.

BACKGROUND

The American Cancer Society estimates over 226,160 new cases of lung cancer and approximately 160,340 lung cancer deaths in 2012, making it the most common cause of malignancy-related mortality in the United States.[1] Non-small cell lung cancer (NSCLC) carries a dismal prognosis with a five-year survival rates estimated to be less than 16%. Poor survival is due, in part, to the fact that 85% of lung cancer cases are diagnosed after metastatic disease progression, when curative treatment options are no longer available. Diagnosis of NSCLC before the development of extensive locoregional or distant metastases promises to improve five-year survival rates to 60% to 80%.[2] Efforts have been made since the early 1970s to identify screening methods for early detection of NSCLC. Unfortunately, neither chest radiography nor sputum cytology was proven effective.[3-8] Single-arm prospective uncontrolled studies on low-dose computed tomography (LDCT) of the chest screening yielded conflicting results.[1, 7] Recently, the National Lung Screening Trial (NLST) demonstrated a 20% relative reduction in lung cancer mortality with LDCT screening of "high-risk" subjects compared to annual chest X-ray (CXR) with a median follow-up of 6.5 years.[8] High-risk was defined by this study to be individuals age 55-74 year old and having greater than 30 pack-year smoking history and having quit less than 15 years prior to randomization.

The approach to indeterminate LDCT screen-detected lung nodules in high-risk populations can represent significant challenges for the clinician. Data from the NLST showed that 24.2% of screening LDCT scans were positive, with 96.4% of these nodules determined to be false positives.[8] An individual has an incidence of 33% of a false-positive LDCT scan after two rounds of annual screening and 7% of these individuals will have unnecessary invasive procedures to prove benign disease.[9] Avoidance of these unnecessary invasive procedures would benefit subject safety. The analysis for the cost-effectiveness of LDCT screening has not been reported by the NLST at this time; however, estimates from other groups have concluded the added cost of LDCT screening for lung cancer to approximate $1.3 billion to $2.0 billion, annually.[9] In addition, it is estimated to cost $240,000 per one life saved by LDCT screening.[9] Decreasing the cost of LDCT screening by decreasing the need for subsequent invasive thoracic procedures or continued radiographic follow-up is paramount.

The potential of individual serum biomarkers to predict malignancy in indeterminate lung nodules has been researched and met with limited success. Published data on individual serum biomarkers, most notably cytokeratin 19 fragment (CYFRA) 21.1, carcinoembryonic antigen (CEA), and tissue plasminogen activator in non-small cell lung cancer (NSCLC) show limited sensitivity and specificity, particularly in early-stage disease.[10, 11] What is needed to improve the efficacy and cost-effectiveness of the LDCT screening paradigm is a biomarker panel for assigning clinical significance to indeterminate lung nodules that may be used as a companion test to help assign clinical significance to LDCT-detected indeterminate lung nodules or provide a risk of malignancy. What is also needed is a biomarker panel assigning risk for the presence of lung cancer as a primary screen, possibly to indicate who should have further diagnostics (like LDCT imaging or biopsy) performed.

BRIEF SUMMARY

A method and a kit for assessing risk of lung cancer versus benign disease in a subject are provided. The method includes obtaining a biological sample from the subject and determining a measurement for a panel of biomarkers in the biological sample. The panel includes at least two biomarkers selected from the group consisting of IL-6, IL-1ra, IL-10, SDF-1α+β, TNF-α, MIP-1α, sIL-2Rα, CA-125, sE-Selectin, Eotaxin, sEGFR, MMP-2, OPN, MCP-1, CRP, sICAM-1 and CYFRA 21.1. The method further includes comparing the measurement to a reference profile for the panel of biomarkers, sorting the patient into a group and determining whether the subject is at risk for lung cancer based on the group.

BRIEF DESCRIPTION OF THE DRAWINGS

FIG. 4 illustrates variable selection using Random Forests of the 17 biomarker candidates. (Abbreviations for FIG. 4: IL-6, Interleukin-6; IL-1ra, Interleukin 1 receptor antagonist; IL-10, Interleukin 10; SDF-1a+b, Stromal cell-derived factor 1a+b; TNF-α, Tumor necrosis factor alpha; MIP-1α, Macrophage inflammatory protein 1 alpha; sIL-2Rα, Soluble interleukin 2 receptor antagonist; CA-125, Cancer antigen 125; sE-Selectin, Soluble endothelial selectin (CD62E); Eotaxin, sEGFR, Soluble epidermal growth factor receptor; MMP-2, Matrix metalloproteinase 2; OPN, Osteopontin; MCP-1, Monocyte chemotactic protein 1; CRP, C-reactive protein; and sICAM-1, soluble intercellular adhesion molecule 1. OOB, out-of bag.

DETAILED DESCRIPTION

Figure 1:
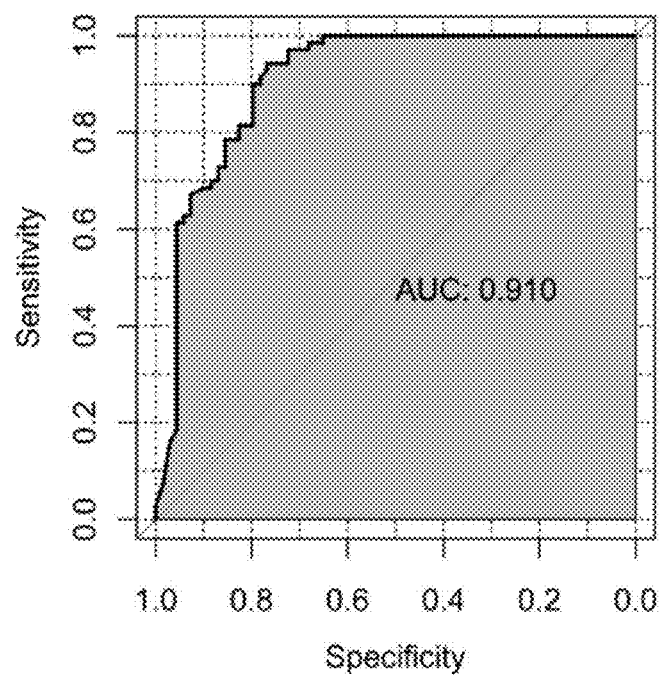
FIG. 1 illustrates receiver operator characteristics curves for a seven biomarker panel in the RUMC discovery cohort. Area under the curve=0.910 with a sensitivity of 100% and specificity of 52.2%.

The present invention will utilize a panel of biomarkers measured in a biological sample obtained from a subject to identify subjects having lung cancer or to assess clinical significance to CT-detected indeterminate lung nodules. In some embodiments, the panel of biomarkers measured may be used to identify subjects having NSCLC or benign disease, possibly as a probability score or assignment of 'risk'.

The term "biomarker" as used herein, refers to any biological compound that can be measured as an indicator of the physiological status of a biological system. A biomarker may comprise an amino acid sequence, a nucleic acid sequence and fragments thereof. Exemplary biomarkers include, but are not limited to cytokines, chemokines, growth and angiogenic factors, metastasis related molecules, cancer antigens, apoptosis related proteins, proteases, adhesion molecules, cell signaling molecules and hormones.

"Measuring" or "measurement" means assessing the presence, absence, quantity or amount (which can be an effective amount) of a given substance within a sample, including the derivation of qualitative or quantitative concentration levels of such substances, or otherwise evaluating the values or categorization of a subject's clinical parameters. Alternatively, the term "detecting" or "detection" may be used and is understood to cover all measuring or measurement as described herein.

The term "high-risk" is assessed according to NLST guidelines. (See Abele et al.)[8]

The terms "sample" or "biological sample" as used herein, refers to a sample of biological fluid, tissue, or cells, in a healthy and/or pathological state obtained from a subject. Such samples include, but are not limited to, blood, bronchial lavage fluid, sputum, saliva, urine, amniotic fluid, lymph fluid, tissue or fine needle biopsy samples, peritoneal fluid, cerebrospinal fluid, nipple aspirates, and includes supernatant from cell lysates, lysed cells, cellular extracts, and nuclear extracts. In some embodiments, the whole blood sample is further processed into serum or plasma samples. In some embodiments, the sample includes blood spotting tests.

The term "subject" as used herein, refers to a mammal, preferably a human.

Biomarker Panel

Biomarkers that may be used include but are not limited to cytokines, chemokines, growth and angiogenic factors, metastasis related molecules, cancer antigens, apoptosis related proteins, proteases, adhesion molecules, cell signaling molecules and hormones. In some embodiments, the biomarkers may be proteins that are circulating in the subject that may be detected from a fluid sample obtained from the subject.

In some embodiments, the biomarker panel may include 2, 3, 4, 5, 6, 7, 8, 9, 11, 14 or 17 biomarkers. In some embodiments, the biomarker panel may include ten or fewer biomarkers. In yet other embodiments, the biomarker panel may include 2, 3, 6 or 7 biomarkers. In some embodiments, the biomarker panel may be optimized from a candidate pool of biomarkers. By way of non-limiting example, the biomarker panel may be optimized for determining whether a subject has a specific disease. In some embodiments, the biomarker panel may be optimized to determine whether the subject has lung cancer and in some embodiments, the lung cancer may be NSCLC. The biomarker panel may be optimized for differentiating between NSCLC from benign disease using a candidate biomarker panel starting with seventeen candidate biomarkers selected from the group including Interleukin 1 receptor antagonist (IL-1ra), Interleukin 10, (IL-10), Cancer antigen 125 (CA-125), Soluble endothelial selectin (CD62E) (sE-Selectin), Tumor necrosis factor alpha (TNF-α), Soluble epidermal growth factor receptor (sEGFR), Macrophage inflammatory protein 1 alpha (MIP-1α), Stromal cell-derived factor 1a+b (SDF-1α+ β), Osteopontin (OPN), C-reactive protein (CRP), Matrix metalloproteinase 2 (MMP-2), Monocyte chemotactic protein 1 (MCP-1), Soluble intercellular adhesion molecule 1 (sICAM-1), Cytokeratin 19 fragment (CYFRA 21.1), Interleukin 6 (IL-6), Eotaxin, and Soluble interleukin 2 receptor antagonist (sIL-2Rα). (See Table 3.)

Biomarker Panel Measurement

Measurement of a biomarker panel generally relates to a quantitative measurement of an expression product, which is typically a protein or polypeptide. In some embodiments, the measurement of a biomarker panel may relate to a quantitative or qualitative measurement of nucleic acids, such as DNA or RNA. The measurement of the biomarker panel of the subject detects differences in expression in subjects having lung cancer compared to subjects that are free from cancer. The expression levels of each individual biomarker may be higher or lower in the subjects having lung cancer compared to subjects that are free from cancer. A panel of a plurality of biomarkers provides an improved predictive value relative to a single biomarker.

Expression of the biomarkers may be measured using any method known to one skilled in the art. Methods for measuring protein expression include, but are not limited to Western blot, immunoprecipitation, immunohistochemistry, Enzyme-linked immunosorbent assay (ELISA), Radio Immuno Assay (RIA), radioreceptor assay, proteomics methods (such as mass spectrometry), or quantitative immunostaining methods. Methods for measuring nucleic acid expression or levels may be any techniques known to one skilled in the art. Expression levels from the panel of biomarkers are measured in the subject and compared to the levels of the panel of biomarkers obtained from a cohort of subjects described below.

In some embodiments, Luminex-based xMAP® multiplexed immunoassays may be used to determine the expression levels of the panel of biomarker. (Luminex Corp.; Austin, Tex.) The Luminex system uses microspheres in a ninety-six well microplate. Each microsphere is dyed with red and infrared fluorophores at a range of independently varied concentrations of dye, creating unique absorbance signatures for each set of microspheres. Each of the microspheres is derivatized with antibodies having binding affinity for a particular type of molecular species. The subject sample is applied to a set of microspheres having different absorbance signatures, each carrying antibodies specific for a particular antigen. The antibodies on the beads then bind to the antigens present in the subject's sample. A secondary antibody may be applied in this system, followed by a streptavidin conjugated fluorophore reporter.

The beads, with their bound antigen and reporter are then sampled by an instrument. A detection chamber is used to detect the unique absorbance signatures and reporter fluorescence intensity, thereby identifying to which set of analytes each microsphere belongs, thus identifying each biomarker tested, and producing a quantitative fluorescent signal from the reporter. The fluorescence intensity of the observed signal is proportional to the quantity of antigen bound to the antibodies on the particular bead. Thus, it is possible to calculate the quantity of a particular biomarker in a sample.

In some embodiments, a kit may be provided with reagents to measure at least two of the a panel of biomarkers. The panel of biomarkers to be measured with the kit may include two or more biomarkers from the group including Interleukin 1 receptor antagonist (IL-1 ra), Interleukin 10, (IL-10), Cancer antigen 125 (CA-125), Soluble endothelial selectin (CD62E) (sE-Selectin), Tumor necrosis factor alpha (TNF-α), Soluble epidermal growth factor receptor (sEGFR), Macrophage inflammatory protein 1 alpha (MIP-1α), Stromal cell-derived factor 1a+b (SDF-1α+β), Osteopontin (OPN), C-reactive protein (CRP), Matrix metalloproteinase 2 (MMP-2), Monocyte chemotactic protein 1 (MCP-1), Soluble intercellular adhesion molecule 1 (sICAM-1), Cytokeratin 19 fragment (CYFRA 21.1), Interleukin 6 (IL-6), Eotaxin, and Soluble interleukin 2 receptor antagonist (sIL-2Rα). The kit may include reagents to measure a panel of biomarkers that includes two, three, four, five, six, seven or more biomarkers combined together to measure a subject's biomarker panel. The kit may be provided with one or more assays provided together in a kit. By way of non-limiting example, the kit may include reagents to measure the biomarkers in one assay. In some embodiments, the kit may include reagents to measure the biomarkers in more than one assay. Some kits may include a 4-plex assay and a 2-plex assay while other kits may include different combinations of assays to cover all the biomarkers needed to be measured. The kit may also include reagents to measure a biomarker individually and other biomarkers in a 2-, 4-, or 8-plex assay. Any combination of reagents and assay may be combined in a kit to cover all the biomarkers needed.

Analysis of Biomarker Panel Measurements

In some embodiments, methods determining whether a subject is at risk for lung cancer is based upon the biomarker panel measurement compared to a reference profile that can be made in conjunction with a statistical algorithm used with a computer to implement the statistical algorithm to sort the subject into a group. In some embodiments, the statistical algorithm is a learning statistical classifier system. The learning statistical classifier system can be selected from the following list of non-limiting examples, including Random Forest (RF), Classification and Regression Tree (CART), boosted tree, neural network (NN), support vector machine (SVM), general chi-squared automatic interaction detector model, interactive tree, multiadaptive regression spline, machine learning classifier, and combinations thereof.

In some embodiments, the Random Forest algorithm may be used to identify the panel of biomarkers. The optimal multivariate panel of biomarkers was chosen based on variable selection algorithms performed within the random forests package in R.[27,28] Liberal inclusion criteria were applied for the individual biomarkers (a Mann-Whitney p value smaller than 0.05 or an area under the ROC curve [AUC] higher than 0.60) to ensure that no biomarker with potential value in a multianalyte panel was prematurely excluded from this selection process based on a weak individual performance. Briefly, the Random Forests package selects optimal combinations of biomarkers by growing numerous (1000 in the present study) cross-validated classification trees for each subpanel of biomarkers, with each tree used to predict group membership for each case. These are counted as the tree votes for that group. The forest chooses the group membership having the most votes over all the trees in the forest. Each such tree is grown by cross-validation; where a training set (approximately two-thirds of the values) is randomly selected from the full data and each tree is grown on this training data to the largest extent possible (no pruning). The resultant tree is then used to predict the group membership for the remaining test cases, which is termed as an out-of-bag (OOB) prediction. This process is then repeated 1000 times; that is, another training set is randomly selected and a new tree is grown and used to perform another OOB prediction. The classification accuracy of the random forest is measured by the averaged error of the OOB predictions across the entire forest; this is termed the OOB error rate. The OOB error thus uses disjoint subsets of the data for model fitting and validation repeatedly. This cross-validation is also used to compute a variable importance for each biomarker included in the Random Forest analysis. The stepwise selection method sequentially searches for optimal subpanel of markers where the marker with the lowest variable importance score from the Random Forest are removed at each step. In some embodiments, the subject data set may include about 20, 30, 40, 50, 60, 70, 80, 90, 100, 110, 120, 130, 140, 150 or more subjects. In some embodiments, the subject data set may be about 100 subjects, about 50 having lung cancer and about 50 having benign disease. In some embodiments, the subject data set may be between about 130-140 subjects with about half the data set having lung cancer and about half the training set having benign disease. Other numbers of subjects in a data set may also be used in the training set. Two thirds of the data set randomly selected may be used for training and the remaining one third tests the algorithm and this process is repeated to select the optimum biomarkers generate a reference profile and to determine whether a subject has cancer.

In some embodiments, a Classification and Regression Tree (CART) algorithm may also be used. The optimal panel of biomarkers resulting from the Random Forest variable selection process may then be used by a CART algorithm to model a classification tree for identifying a subject's true (pathologic) preoperative lymph node status. This analysis was performed using the RPART package of the R statistical software suite.[29] Briefly, classification trees determine a set of binary if-then logical (split) conditions that permit accurate classification of (in this case) the subject's nodal status. The CART algorithm discriminates between groups by splitting the range of values measured for each individual biomarker at all of its possible split points. The 'goodness of split criterion' is then used to determine the best split point for each biomarker for predicting nodal status. CART then ranks all of the best splits on each biomarker and selects the best biomarker and its split point for the split at the root node. CART then assigns classes to the two split nodes according to a rule that minimizes misclassification error. This process is continued at each nonterminal child node and at each of the successive stages until all observations are perfectly classified or the sample size within a given node is too small to divide (n a user-supplied number; such as 5). The final output of the resulting classification tree is a graphical display of decision criteria for each split, with the resulting predicted group memberships at the terminal nodes. The predicted probabilities of preoperative nodal status from the tree were used to obtain sensitivity and specificity across a range of cut-points for decision rules and the resulting ROC curve.

Subject Cohorts

Between 2004 and 2010, 136 subjects at Rush University Medical Center (RUMC) were enrolled and divided into the following cohorts: a) pathologically diagnosed lymph-node negative lung cancer (n=69), and b) benign disease (n=67). All stage classifications were according to the 7$^{th}$ edition criteria[12,13] and were pathologically confirmed. Subjects with benign resected disease (n=35) were diagnosed with granulomatous inflammation (n=21), non-specific inflammatory changes (n=9), and lung infections (n=5). The remaining subjects comprising our benign cohort were part of an internal screening program with LDCT determined benign disease (n=32). Inclusion criteria for individuals enrolled in our screening program were age greater than 50 years old or smoking history greater than 20 pack years. All participants were followed with annual LDCT and remained cancer free for a minimum 2 year follow-up. Demographic information for these subject groups are contained in Table 1.

TABLE 1

Demographics for the discovery population from Rush University Medical Center.

| | | Benign Screening | Benign Resected | Lung Cancer |
|---|---|---|---|---|
| Gender | Male | 14 (44) | 19 (54) | 29 (42) |
| | Female | 18 (56) | 16 (46) | 40 (58) |
| Age[a] | Median | 61 | 65 | 67 |
| | Range | 51-82 | 20-80 | 48-83 |
| Smoking History[b] | Median | 36 | | 35 |
| | Non-smoker | 6-126 | 0-60 | 0-120 |
| Nodule Size[c] | Median | 4 | 14 | 18 |
| | Range | 2-17 | 4-75 | 7-175 |
| TNM | $T_1N_0M_0$ | | | 51 |
| | $T_2N_0M_0$ | | | 13 |
| | $T_3N_0M_0$ | | | 2 |
| | $T_4N_0M_0$ | | | 0 |
| Histologic Diagnosis | Adenocarcinoma | | | 49 (72) |
| | Squamous Cell | | | 10 (14) |
| | Neuroendocrine | | | 10 (14) |
| Benign Diagnosis | Granuloma | | 21 (60) | |
| | Inflammation | | 9 (26) | |
| | Infection | | 5 (14) | |

Notes:
[a] age in years;
[b] smoking history in pack-years;
[c] nodule size in millimeters (mm)

The validation population (n=81) consisted of the following cohorts, received from a collaboration with the Mayo Clinic (Rochester, Minn.): a) pathologically diagnosed lymph-node negative lung cancer (n=20), and b) benign disease (n=61). Demographic information is contained in Table 2. All subject data was acquired with written informed consent and in absolute compliance with the Institutional Review Board at either Rush University Medical Center or the Mayo Clinic.

TABLE 2

Demographics for the validation population from the Mayo Clinic.

| | | Benign Resected | Lung Cancer |
|---|---|---|---|
| Gender | Male | 30 (49) | 12 (60) |
| | Female | 31 (51) | 8 (40) |
| Age[a] | Median | 63 | 64 |
| | Range | 30-83 | 49-82 |
| Smoking History[b] | Median | 25 | 35 |
| | Non-smoker | 0-100 | 0-100 |
| Nodule Size[c] | Median | 14 | 22 |
| | Range | 3-50 | 8-80 |
| TNM | $T_1N_0M_0$ | | 14 |
| | $T_2N_0M_0$ | | 5 |
| | $T_3N_0M_0$ | | 1 |
| | $T_4N_0M_0$ | | 0 |
| Histologic Diagnosis | Adenocarcinoma | | 10 (50) |
| | Squamous Cell | | 5 (25) |
| | Neuroendocrine | | 5 (25) |

Notes:
[a] age in years;
[b] smoking history in pack-years;
[c] nodule size in millimeters (mm)

Measurement of Plasma Biomarker Concentrations

Plasma was prepared using standard phlebotomy protocols from peripheral blood collected in yellow top tubes either immediately before an anatomic resection or in conjunction with a lung cancer screening trial. No specimen was subjected to more than two freeze/thaw cycles.[14-17] Seventeen candidate biomarkers were used for discovery based on previously shown success in differentiating NSCLC from benign disease.[15] Assays for CA-125, CYFRA 21-1, osteopontin (OPN), SDF-1($\alpha$+$\beta$) (Millipore, Billerica, Mass., USA) were measured as a 4-plex assay kit; IL-1 ra, sIL-2R$_\alpha$, IL-6, IL-10, Eotaxin, MCP-1, MIP-1$\alpha$, TNF-$\alpha$ (Millipore, Billerica, Mass., USA) as an 8-plex assay kit; and sE-Selectin, sICAM-1 (Millipore, Billerica, Mass., USA) as a 2-plex assay kit. The remaining plasma biomarkers (Millipore, Billerica, Mass., USA) were run individually and consist of sEGFR, MMP-2, and CRP. All biomarker concentrations were calculated using a five-parametric curve fit using xPONENT v4.0.3 (Luminex Corp.; Austin, Tex.) in a blinded fashion using data collected on a Luminex FlexMAP 3D system. Table 3 lists the 17 biomarkers evaluated in this study.

TABLE 3

All biomarkers analyzed for all patients in the RUMC discovery population

| | | Univariate Statistics | |
|---|---|---|---|
| Biomarker | Abbreviation | p-value[a] | AUC |
| Interleukin 1 receptor antagonist | IL-1ra | <0.001 | 0.909 |
| Interleukin 10 | IL-10 | 0.001 | 0.742 |
| Cancer antigen 125 | CA-125 | 0.001 | 0.728 |
| Soluble endothelial selectin (CD62E) | sE-Selectin | 0.002 | 0.696 |
| Tumor necrosis factor alpha | TNF-$\alpha$ | 0.011 | 0.673 |
| Soluble epidermal growth factor receptor | sEGFR | 0.016 | 0.644 |
| Macrophage inflammatory protein 1 alpha | MIP-1$\alpha$ | 0.018 | 0.640 |
| Stromal cell-derived factor 1 a + b | SDF-1$\alpha$ + $\beta$ | 0.029 | 0.658 |
| Osteopontin | OPN | 0.074 | 0.647 |
| C-reactive protein | CRP | 0.209 | 0.576 |
| Matrix metalloproteinase 2 | MMP-2 | 0.324 | 0.548 |
| Monocyte chemotactic protein 1 | MCP-1 | 0.378 | 0.539 |
| Soluble intercellular adhesion molecule 1 | sICAM-1 | 0.690 | 0.546 |
| Cytokeratin 19 fragment | CYFRA 21.1 | 0.783 | 0.520 |
| Interleukin 6 | IL-6 | 0.868 | 0.538 |
| Eotaxin | Eotaxin | 0.972 | 0.521 |
| Soluble interleukin 2 receptor antagonist | sIL-2R$_\alpha$ | 1.000 | 0.508 |

Note:
[a] Mann-Whitney Rank Sum test (2-sided)

Statistical Methods

Methods for candidate biomarker testing were consistent with those previously reported by our group.[14-17] Descriptive statistics were obtained along with receiver operator characteristics (ROC) parameters (including "area under the curve" (AUC)) to assess the performance of the 17 individual candidate biomarkers using SPSS 18.0 for Windows (SPSS Inc., Chicago, Ill., USA). The Mann-Whitney rank sum test was used to evaluate differences in biomarker concentrations. A threshold for significance as a biomarker was set to an AUC of greater than 0.60 or a Mann-Whitney rank sum (two-sided) p-value less than 0.05. The optimal multivariate panel was selected using variable selection based on importance scores from the Random Forests method as discussed above. Sensitivity, specificity and negative predictive value were used to evaluate performance of our biomarker panel. The biomarker panel selected based on data from the RUMC discovery cohort was then used to make predictions of disease in the validation cohort (Mayo Clinic, Rochester, Minn.) in a blinded fashion (where the statistician is kept completely blinded of the true disease status data in the validation cohort).

Results

The median age of the subjects with benign disease in the RUMC screening cohort was 61 years old while the benign resected cohort's median age was 65 years old (range 20-82). In comparison the median age of subjects in the RUMC lung cancer cohort was 67 years old (range 48-83). The median pack-year smoking history of subjects with benign disease in the RUMC screening cohort was 36 pack-years (range 6-126) while the RUMC benign resected cohort's median smoking history was 1 pack-year (range 0-60). The median pack-year smoking history of the RUMC lung cancer cohort was 35 pack-years (range 0-120). Univariate analysis of the RUMC discovery cohort data using receiver operator characteristics (ROC) curve parameters revealed nine biomarkers of the seventeen tested with an AUC>0.60, and eight biomarkers to be significantly different in indeterminate nodules between the lung cancer and the benign disease groups, as shown in Table 3. Four biomarkers showed strong significance (p<0.01) for identifying lung cancer in indeterminate nodules and include IL-1ra, IL-10, CA-125 and sE-Selectin. All four biomarkers were shown to be significantly elevated in subjects with lung cancer.

Multivariate analysis of the data from only the RUMC discovery cohort subjects using variable selection based on Random Forests method resulted in a 7-analyte panel including IL-6, IL-10, IL-1 ra, sIL-2R$_\alpha$, SDF-1$\alpha$+$\beta$, TNF-$\alpha$, and MIP-1$\alpha$. This Random Forest generated panel differentiated subjects with NSCLC from subjects with benign disease with a cross-validated accuracy of 76.5%. This panel provided 35 cases of true negatives, 69 cases of true positives, 32 cases of false positives, and 0 cases of false negatives for a calculated sensitivity of 100%, specificity of 52.2%, and a negative predictive value of 100%. The area under the curve was calculated to be 0.910 (see FIG. 1).

Figure 2:
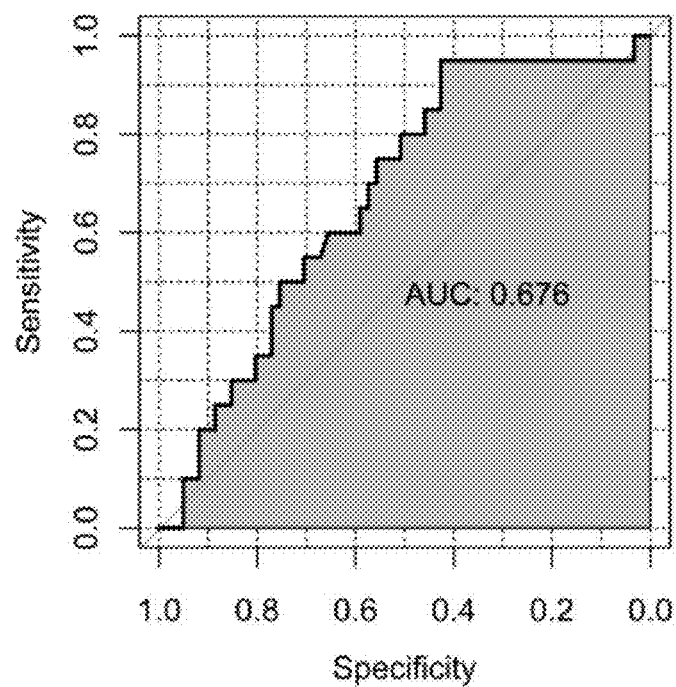
FIG. 2 illustrates receiver operator characteristics curves for the seven biomarker panel in the Mayo Clinic validation cohort. Area under the curve=0.676 with a sensitivity of 95.0% and specificity of 24.6%.
Figure 3A:
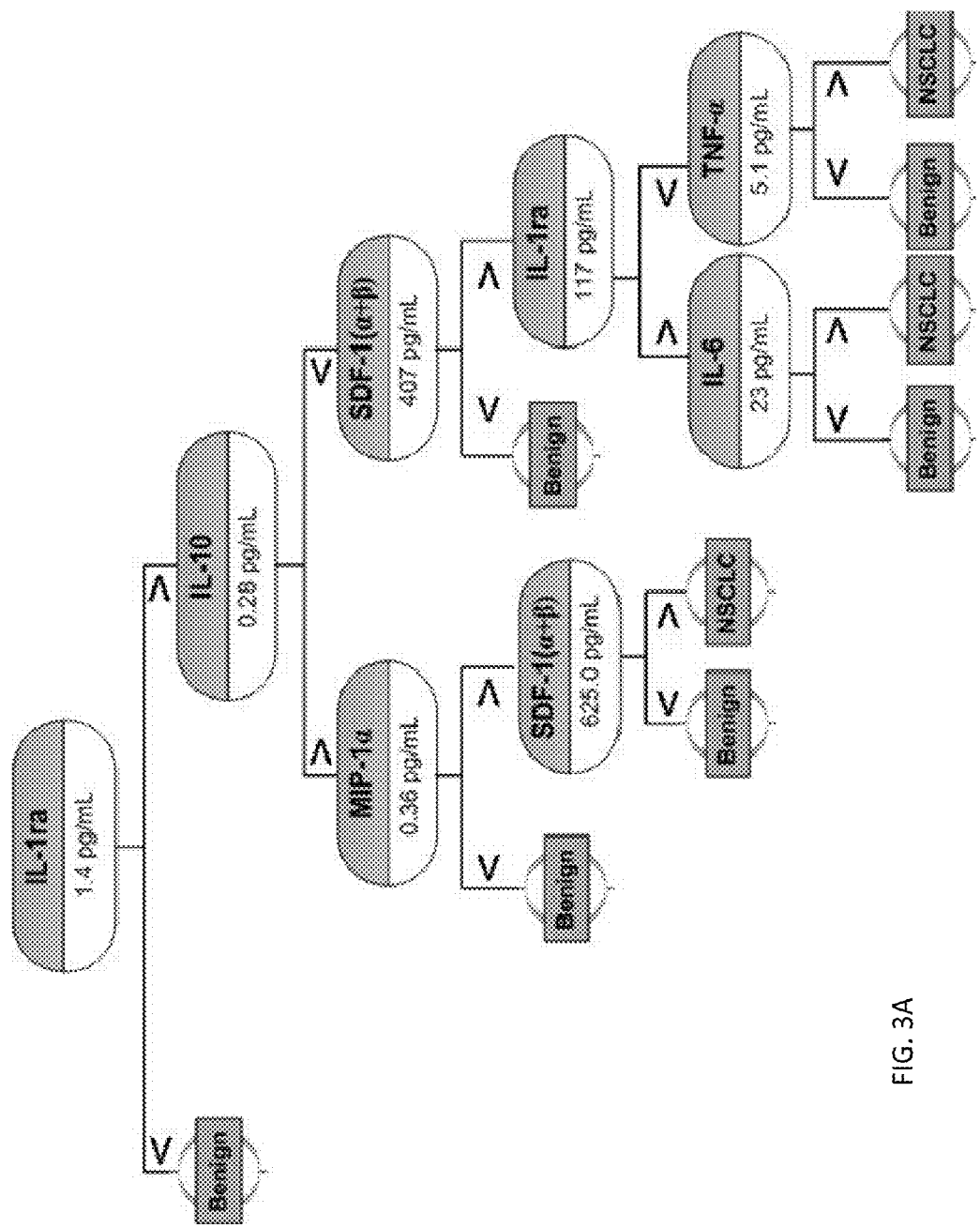
FIGS. 3A-3D illustrate exemplary Random Forest Trees generated using the RUMC discovery cohort.
Figure 3B:
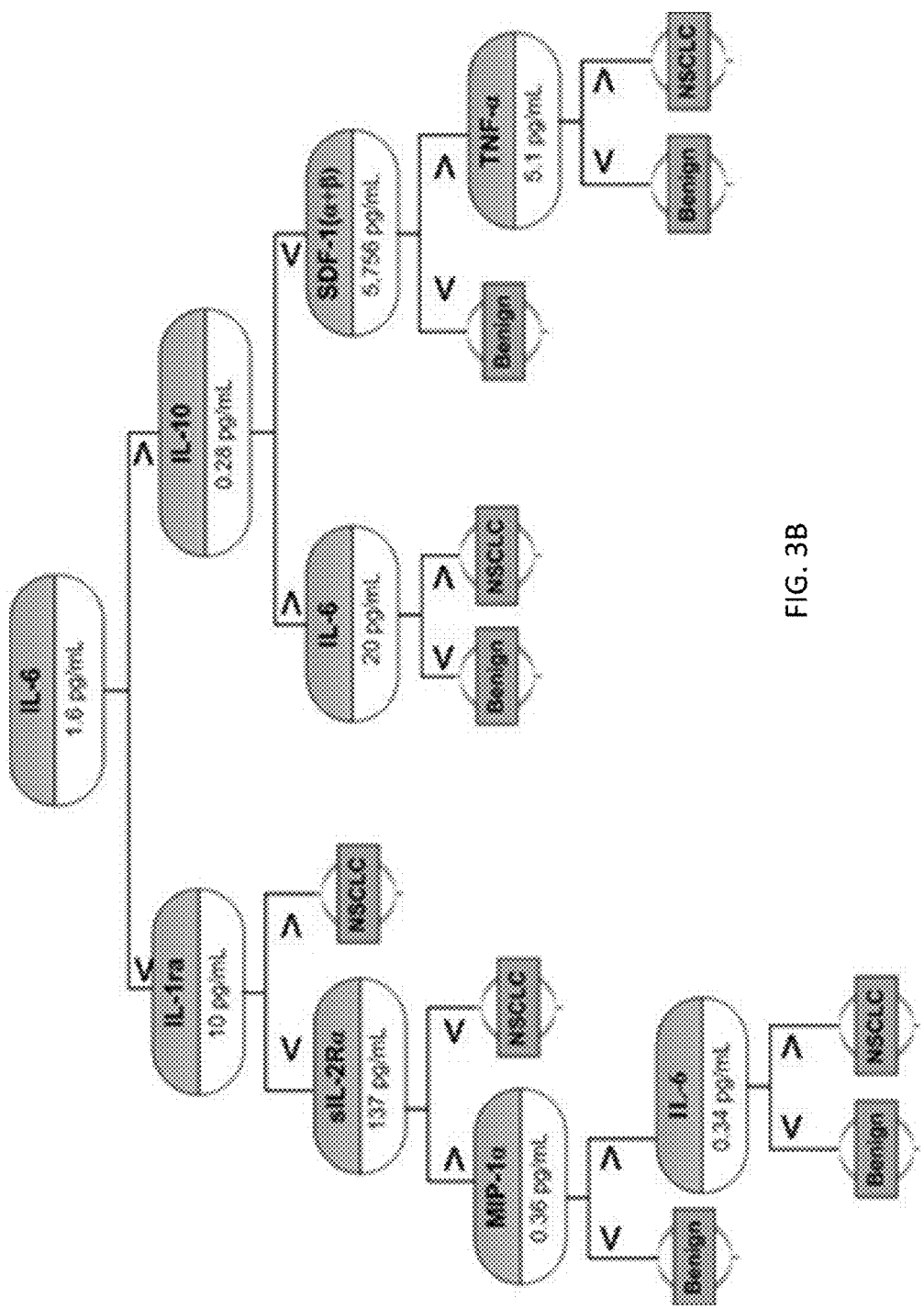
Figure 3C:
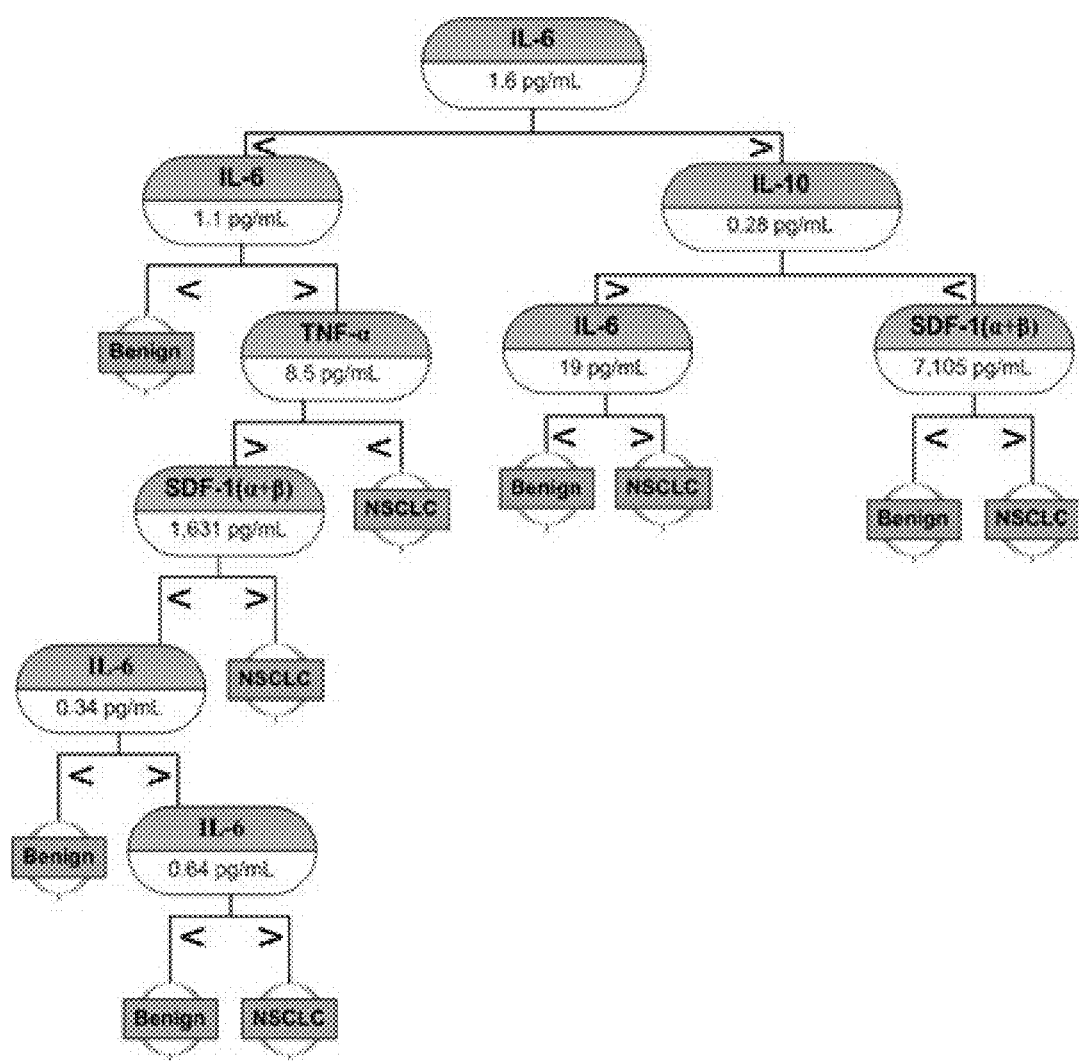
Figure 3D:
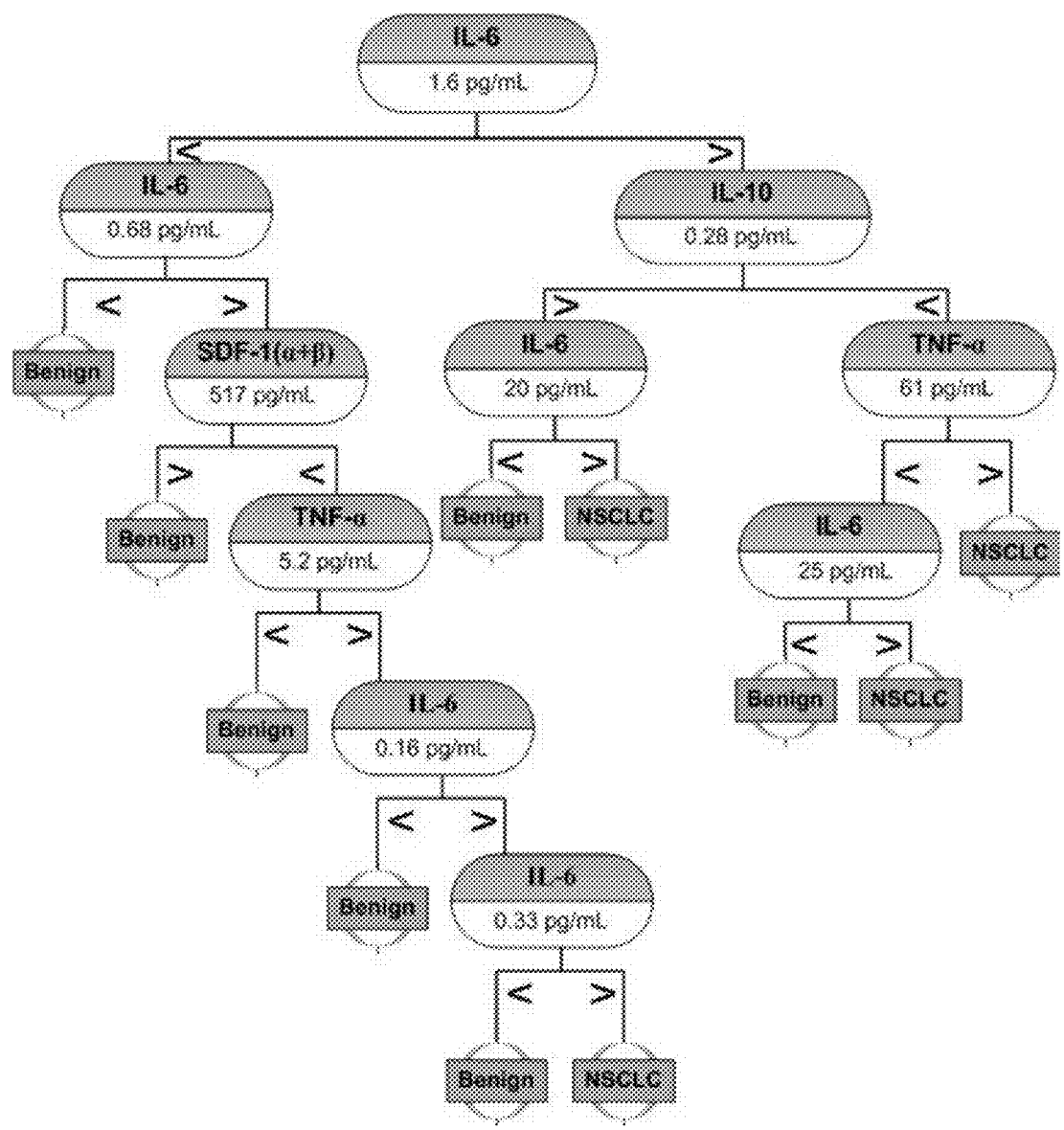

The Random Forest generated 7-analyte panel developed on the RUMC Cohort was then used to predict the disease status in the validation cohort from the Mayo Clinic in a blinded fashion. The panel differentiated subjects with lung cancer (n=20) from subjects with benign disease (n=61) with an accuracy of 42.0%. This panel provided 15 cases of true negatives, 19 cases of true positives, 46 cases of false positives, and 1 case of false negatives for a calculated sensitivity of 95.0%, specificity of 24.6%, and a negative predictive value of 93.8%. The area under the curve was calculated to be 0.676 (see FIG. 2).

Additional panels may be used to determine whether a subject has lung cancer or benign disease. FIG. 4 illustrates 10 different panels generated from 17 biomarker candidates using variable selection by a Random Forest algorithm. The averaged OOB misclassification errors from the range of the 1000 trees of the Random Forest grown for each of the panels shown in FIG. 4 is shown. Each of the panels shown has a misclassification error of less than 20% and panels numbered 2-10 have a misclassification error of less than 15%. Panels having a misclassification error of less than 20% may be used to determine the whether a subject has lung cancer or benign disease. In some embodiments, biomarker panels have a misclassification error of less than 14%, less than 13% or less than 12% may be used.

The primary goal of LDCT screening programs is to detect asymptomatic disease in subjects at "high-risk" for lung cancer, therefore, increasing eligibility for surgical intervention with curative-intent and greatly improving prognosis. Currently, an estimated 7 million individuals in the United States qualify for lung cancer screening, based on the NLST inclusion criteria.[8] If CT-based screening protocols were implemented today, the healthcare system would be burdened by the 1.6 to 3.5 million indeterminate nodules identified by LDCT screening.[19, 20] Under current guidelines, positive screening LDCT scans are stratified by nodule size to determine lung cancer risk and diagnostic recommendations. Nodules less than 4 mm, 4-6 mm, and 6-8 mm are recommended to be followed by LDCT screening at annual, 6 month and 3 month intervals, respectively.[18] Nodules greater than 8 mm should be investigated further with PET scan and/or biopsy. A significant number of subjects will undergo invasive procedures to further characterize these indeterminate nodules, and according to the NLST data, 96% of those nodules will prove to be benign.

As a result of the NLST trial, the International Association for the Study of Lung Cancer (IASLC) recently published a position statement with regards to LDCT screening.[21] The IASLC appointed a Strategic CT Screening Advisory Committee (SSAC) to deliver guidelines and recommendations in six key areas of LDCT screening. One specific focus of the SSAC was to develop guidelines for the clinical work-up of "indeterminate nodules" resulting from LDCT screening. Within these guidelines the IASCL-SSAC recognized the need for further investigation of biomarkers as a complement to address the high number of false positive cases with LDCT screening.[21] With successful discovery of biomarkers capable of increasing the efficacy of LDCT screening, LDCT screening can evolve into a universally available tool for clinicians.

The biomarker panels identified in FIG. 4 above refined previous efforts made by our group to develop a serum biomarker panel capable of assigning risk of NSCLC versus benign disease.[14-17] Significant biomarkers were evaluated which previously showed value in serum for predicting NSCLC versus benign disease and these biomarkers were used to determine value in plasma for assigning risk for NSCLC versus benign disease in subjects with indeterminate nodules. Large national cancer repositories have focused efforts to store plasma for the development and validation of biomarker panels.[23] As a result, the use of plasma as the matrix for discovery and validation is crucial for future validations. One plasma biomarker panel useful for determination NSCLC versus benign disease includes IL-6, IL-10, IL-1ra, sIL-21R$_\alpha$, SDF-1$\alpha$+$\beta$, TNF-$\alpha$ and MIP-1$\alpha$. This seven analyte plasma panel biomarker shares three analytes (IL-1R$_\alpha$, TNF-$\alpha$, MIP-1$\alpha$) with our previous serum biomarker panel used for predicting NSCLC versus benign disease.[15] The seven analyte plasma biomarker panel was able to predict lung cancer versus benign disease in our discovery cohort with an accuracy of 76.5%. Our panel accuracy was affected by a larger than expected number of false positive cases (n=32). The clinical value of our plasma biomarker panel is its ability to effectively rule out lung cancer in subjects with indeterminate nodules when the panel predicts benign disease (negative predictive value). The negative predictive value of our plasma biomarker test was 100% in our discovery cohort, with no false negative cases observed. The observed high sensitivity (100%) and high negative predictive value (100%) of our plasma biomarker panel in our discovery cohort was suspect for apparent "overfitting" of the data, despite attempts to avoid this bias with Random Forest multivariate analysis. Validation studies demonstrated this was not the case, however.

Few other blood tests seem ready for clinical use for assigning clinical significance to indeterminate nodules. Two such panels include the EarlyCDT-Lung test manufactured by Oncimmune, Limited[24, 25] and a multi-analyte serum biomarker panel by Bigbee and colleagues.[26] The EarlyCDT-Lung test consists of autoantibodies against p53, NY-ESO, cancer-associated antigen (CAGE), GBU4-5, annexin I, and SOX2, and has been extensively tested and validated against early-stage lung cancer subjects and control subjects.[24, 25] However, clinical validation of this test provides an average sensitivity of 39% and specificity of approximately 90%. More recently, Bigbee et al. reported the validation of an 11-analyte serum biomarker panel for predicting the level of cancer risk in high-risk individuals with indeterminate lung nodules.[26] This serum biomarker panel consisted of prolactin, transthyretin, thrombospondin-1, sE-selectin, C—C motif chemokine 5, macrophage migration inhibitory factor (MIF of GIF), plasminogen activator inhibitor (PAI-1), tyrosine-protein kinase, erbb-2, cytokeratin fragment 19, and serum amyloid A (SAA). The serum biomarker panel achieved a sensitivity and specificity of 73.3% and 93.3% respectively in their validation cohort.[26] The positive predictive value of the published serum panel was an impressive 92.3%, however, this feature will have a modest clinical impact due to the fact that confirming cancer in these subjects does not change the treatment plan; all will receive subsequent invasive procedures regardless. Alternatively, the negative predictive value of the Bigbee et al. serum biomarker panel in validation studies was very good at 77.8% and will help clinical management of a screening population.

A test with a negative predictive value has been shown that will allow clinicians to confidently rule-out malignancy in indeterminate pulmonary nodules found during LDCT screening. In addition to the cost advantage to the healthcare system this assay may offer, the rapid result capability (less than 24 hours) will reduce subject anxiety inherent to current diagnostic methods, which may take as long as 6 months to complete.

The practice of the present invention will employ, unless otherwise indicated, conventional methods for measuring the level of the biomarker within the skill of the art. The techniques may include, but are not limited to, molecular biology and immunology. Such techniques are explained fully in the literature. See, e.g., Sambrook, et al. Molecular Cloning: A Laboratory Manual (Current Edition, Cold Spring Harbor Laboratory Press, Cold Spring Harbor, N.Y.); Current Protocols in Molecular Biology (Eds. A Ausubel et al., NY: John Wiley & Sons, Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition).

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

REFERENCES

1. Henschke C I, Yankelevitz D F, Libby D M, et al. Survival of patients with stage I lung cancer detected on CT screening. *N Engl J Med* 2006; 355:1763-1771.
2. Port J L, Kent M S, Korst R J, et al. Tumor size predicts survival within stage IA non-small cell lung cancer. *Chest* 2003; 124:1828-1833.
3. Fontana R S, Sanderson D R, Woolner L B, et al. Lung cancer screening: the Mayo program. *J Occup Med* 1986; 28:746-750.
4. Kubik A, Parkin D M, Khlat M, et al. Lack of benefit from semi-annual screening for cancer of the lung: follow-up report of a randomized controlled trial on a population of high-risk males in Czechoslovakia. *Int J Cancer* 1990; 45:26-33.
5. Melamed M R, Flehinger B J, Zaman M B, et al. Screening for early lung cancer. Results of the Memorial Sloan-Kettering study in New York. *Chest* 1984; 86:44-53.
6. Oken M M, Hocking W G, Kvale P A, et al. Screening by chest radiograph and lung cancer mortality: the Prostate, Lung, Colorectal, and Ovarian (PLCO) randomized trial. *Jama* 2011; 306:1865-1873.
7. Bach P B, Jett J R, Pastorino U, et al. Computed tomography screening and lung cancer outcomes. *Jama* 2007; 297:953-961.
8. Aberle D R, Adams A M, Berg C D, et al. Reduced lung-cancer mortality with low-dose computed tomographic screening. *N Engl J Med* 2011; 365:395-409.
9. Goulart B H, Bensink M E, Mummy D G, et al. Lung cancer screening with low-dose computed tomography: costs, national expenditures, and cost-effectiveness. *J Natl Compr Canc Netw* 2012; 10:267-275.
10. Buccheri G, Torchio P, Ferrigno D. Clinical equivalence of two cytokeratin markers in mon-small cell lung cancer: a study of tissue polypeptide antigen and cytokeratin 19 fragments. *Chest* 2003; 124:622-632.
11. Pastor A, Menendez R, Cremades M J, et al. Diagnostic value of SCC, CEA and CYFRA 21.1 in lung cancer: a Bayesian analysis. *Eur Respir J* 1997; 10:603-609.
12. Goldstraw P, Crowley J, Chansky K, et al. The IASLC Lung Cancer Staging Project: proposals for the revision of the TNM stage groupings in the forthcoming (seventh) edition of the TNM Classification of malignant tumours. *J Thorac Oncol* 2007; 2:706-714.
13. Groome P A, Bolejack V, Crowley J J, et al. The IASLC Lung Cancer Staging Project: validation of the proposals for revision of the T, N, and M descriptors and consequent stage groupings in the forthcoming (seventh) edition of the TNM classification of malignant tumours. *J Thorac Oncol* 2007; 2:694-705.
14. Borgia J A, Basu S, Faber L P, et al. Establishment of a multi-analyte serum biomarker panel to identify lymph node metastases in non-small cell lung cancer. *J Thorac Oncol* 2009; 4:338-347.
15. Farlow E C, Vercillo M S, Coon J S, et al. A multi-analyte serum test for the detection of non-small cell lung cancer. *Br J Cancer* 2010; 103:1221-1228.
16. Patel K, Farlow E C, Kim A W, et al. Enhancement of a multianalyte serum biomarker panel to identify lymph node metastases in non-small cell lung cancer with circulating autoantibody biomarkers. *Int J Cancer* 2011; 129:133-142.
17. Farlow E C, Patel K, Basu S, et al. Development of a multiplexed tumor-associated autoantibody-based blood test for the detection of non-small cell lung cancer. *Clin Cancer Res* 2010; 16:3452-3462.
18. MacMahon H, Austin J H, Gamsu G, et al. Guidelines for management of small pulmonary nodules detected on CT scans: a statement from the Fleischner Society. *Radiology* 2005; 237:395-400.
19. Bach P B, Silvestri G A, Hanger M, et al. Screening for lung cancer: ACCP evidence-based clinical practice guidelines (2nd edition). *Chest* 2007; 132:69 S-77S.

20. Henschke C I, Yankelevitz D F. CT screening for lung cancer: update 2007. *Oncologist* 2008; 13:65-78.
21. Field J K, Smith R A, Aberle D R, et al. International Association for the Study of Lung Cancer Computed Tomography Screening Workshop 2011 report. *J Thorac Oncol* 2012; 7:10-19.
22. Bach P B, Mirkin J N, Oliver T K, et al. Benefits and harms of CT screening for lung cancer: a systematic review. *Jama* 2012; 307:2418-2429.
23. Patz E F, Jr., Caporaso N E, Dubinett S M, et al. National Lung Cancer Screening Trial American College of Radiology Imaging Network Specimen Biorepository originating from the Contemporary Screening for the Detection of Lung Cancer Trial (NLST, ACRIN 6654): design, intent, and availability of specimens for validation of lung cancer biomarkers. *J Thorac Oncol* 2011; 5:1502-1506.
24. Boyle P, Chapman C J, Holdenrieder S, et al. Clinical validation of an autoantibody test for lung cancer. *Ann Oncol* 2011; 22:383-389.
25. Murray A, Chapman C J, Healey G, et al. Technical validation of an autoantibody test for lung cancer. *Ann Oncol* 2010; 21:1687-1693.
26. Bigbee W L, Gopalakrishnan V, Weissfeld J L, et al. A multiplexed serum biomarker immunoassay panel discriminates clinical lung cancer patients from high-risk individuals found to be cancer-free by CT screening. *J Thorac Oncol* 2012; 7:698-708.
27. Breiman L. Random Forests. *Mach Learn* 2001; 45:5-32.
28. Brieman L, Friedman J, Olshen R, Stone C. Classification and Regression Trees. Belmont, Calif.: Wadsworth Co, 1984.
29. Team R D C. R: A Language and Environment for Statistical Computing. Vienna, Austria: R Foundation for Statistical Computing, 2006.

The invention claimed is:
1. A method of measuring a panel of biomarkers in a subject suspected of having non-small cell lung cancer, the method comprising:
   obtaining a biological sample from the subject;
   determining a measurement for the panel of biomarkers in the biological sample, the panel consisting of IL-6, IL-1ra, IL-10, SDF-1α+β, TNF-α, and MIP-1α, wherein the measurement comprises measuring a level of each biomarker in the panel.
2. The method according to claim 1, comprising determining the measurement for the panel of biomarkers wherein the panel further comprises sIL-2Rα.
3. The method according to claim 1, wherein the measurement is obtained after detection of an indeterminate nodule is found by low-dose computed tomography (LDCT) detection.
4. The method according to claim 1, wherein the measurement is a primary screen.
5. The method according to claim 1, wherein the subject is a "high risk" subject for lung cancer.
6. The method according to claim 1, comprising using a learning statistical classifier system to analyze the measurement of the panel of biomarkers.
7. The method according to claim 6, wherein the learning statistical classifier system is a Random Forest system.
8. The method according to claim 7, wherein the panel has a misclassification error of less than 20%.
9. The method according to claim 6, wherein the Random Forest system comprises 1000 cross-validated classification trees.
10. The method according to claim 1, wherein the biological sample comprises plasma sample or serum sample.

* * * * *